(12) United States Patent
Butterfield (10) Patent No.: US 6,394,771 B2
(45) Date of Patent: May 28, 2002

(54) SYSTEM AND METHOD FOR INCREASED FLOW UNIFORMITY

(75) Inventor: Robert D. Butterfield, Poway, CA (US)

(73) Assignee: Alaris Medical Systems, Inc., San Diego, CA (US)

(*) Notice: Subject to any disclaimer, the term of this patent is extended or adjusted under 35 U.S.C. 154(b) by 0 days.

(21) Appl. No.: 09/794,539

(22) Filed: Feb. 26, 2001

Related U.S. Application Data (63) Continuation of application No. 09/128,302, filed on Aug. 3, 1998, now Pat. No. 6,193,480.

(51) Int. Cl.$^7$ .................................................. F04B 43/08
(52) U.S. Cl. ...................................... 417/477.1; 417/43
(58) Field of Search ................................. 417/477.1, 43, 417/53, 12, 44.1, 45, 300; 318/685; 604/153

(56) References Cited

U.S. PATENT DOCUMENTS

| | | | |
|---|---|---|---|
| 4,346,705 A | 8/1982 | Pekkarinen et al. | |
| 4,653,987 A | 3/1987 | Tsuji et al. | |
| 4,657,486 A | 4/1987 | Stempfle et al. | |
| 4,718,576 A | 1/1988 | Tamura et al. | |
| 4,731,057 A | 3/1988 | Tanaka et al. | |
| 4,795,314 A | 1/1989 | Prybella et al. | |
| 4,909,710 A | 3/1990 | Kaplan et al. | |
| 4,952,124 A | * 8/1990 | Ogami ........................ | 417/474 |
| 5,074,756 A | 12/1991 | Davis | |
| 5,078,683 A | 1/1992 | Sancoff et al. | |
| 5,105,140 A | 4/1992 | Matthews et al. | |
| 5,165,874 A | 11/1992 | Sancoff et al. | |
| 5,213,573 A | * 5/1993 | Sorich et al. ................. | 604/66 |
| 5,716,194 A | * 2/1998 | Butterfield et al. .......... | 417/43 |

* cited by examiner

Primary Examiner—Willis R. Wolfe
Assistant Examiner—Mahmoud Gimie
(74) Attorney, Agent, or Firm—Fulwider Patton Lee & Utecht, LLP (57) ABSTRACT

A system for increasing the volumetric flow uniformity of fluid pumped through a conduit by an infusion pump. A pumping mechanism operates in identifiable step movements that are broken down into microstep movements that are then grouped into packets. The pumping mechanism controls the period of each microstep, so that the sum of the microstep periods in a packet is essentially equal to the packet period, with little or no waiting time on the motor. The motor preferably begins moving the assigned microsteps in each packet immediately upon the beginning of the time period, but controls the period of the microsteps for that packet.

9 Claims, 5 Drawing Sheets

SYSTEM AND METHOD FOR INCREASED FLOW UNIFORMITY

This application is a continuation of application Ser. No. 09/128,302, filed on Aug. 3, 1998, now U.S. Pat. No. 6,193,480.

BACKGROUND

The present invention relates generally to a system and method for controlling the flow of fluids through a conduit, and in particular to controlling a pump acting on a conduit for increasing the uniformity of the fluid flow through the conduit.

In certain systems used for infusing parenteral fluids intravenously to a patient, a pumping mechanism engages a length of conduit or tubing of a flexible administration set to pump the parenteral fluid to the patient at a selected flow rate. A peristaltic pump is one commonly used type of pumping mechanism and employs the sequential occlusion of the administration set tubing to move the fluid through the tubing to the patient.

Linear-type peristaltic pumps typically include a row of adjacent, reciprocating pumping fingers that are sequentially urged against the fluid administration set tubing to occlude adjacent segments of that tubing in a wave-like action to force fluid through the tubing. The reciprocating, sequential motion of the fingers is accomplished in one arrangement by the use of a cam shaft rotated by a drive motor. Disposed along the length of the cam shaft are a plurality of adjacent cams having generally symmetrical lobe geometries with one cam operating each finger. The cams are disposed along the cam shaft so that adjacent lobes project at different angular positions relative to the cam shaft. The fingers in turn advance and retract sequentially in accordance with the angular positions of the respective cam lobes and rotation of the cam shaft.

The drive motor typically comprises a step motor having a certain number of motor steps per complete rotation of its armature; for example, two-hundred steps per 360 degrees of rotation. Typically, a pump cycle is defined as a complete cycle of the pumping mechanism. For example, in the case of a twelve-finger linear peristaltic pump, a pump cycle is complete when all twelve fingers have engaged the fluid conduit and returned to the positions they had at the start of the cycle. In many such systems, when the pump mechanism has completed a full cycle the step motor will have also traveled through 360 degrees of rotation, thereby causing it to have travelled through all of its steps in that rotation.

Each incremental movement of the motor causes a corresponding incremental movement of the cams and fingers and results in a discrete volume of fluid or "step volume" being pumped through the conduit. An inherent characteristic of linear peristaltic pumps is that step volumes vary from other step to step, and at certain points over a pump cycle the step volume may even be negative (i.e., reverse flow). This reverse flow results when the outlet side fingers of the linear peristaltic pump are retracted from the tubing and a reverse flow surge backfills the tubing pumping segment due to a pressure difference between the pumping segment and the downstream segment.

In one effort to increase the flow uniformity within a peristaltic pump cycle, the design of the pumping mechanism was tailored. For example, tailored, non-symmetrical cam lobes have been developed to accelerate, decelerate or limit the advancement of the pumping fingers as they engage and disengage segments of the tubing. Some of these designs have resulted in increased uniformity of volumes pumped per motor step at a particular design flow rate. However, it has been found that the effectiveness of these designs decreases at flow rates that differ significantly from the design flow rate.

Another approach to increasing flow uniformity is described in U.S. Pat. No. 5,716,194 to Butterfield et al., entitled *SYSTEM FOR INCREASING FLOW UNIFORMITY*, the contents of which are incorporated herein by reference. In U.S. Pat. No. 5,716,194, flow uniformity was enhanced by grouping several adjacent steps into larger "supersteps," with each superstep comprised of a group of steps. By carefully grouping of the steps, supersteps can be created in such a way that each superstep has essentially the same volume of fluid as the other supersteps. For example, one superstep may consist of 7 relatively low-volume motor steps, while another superstep may consist of 3 larger-volume motor steps. By associating more of the low-volume motor steps on the first superstep, the total volume of the first superstep approximately equals the total volume of the second superstep. With supersteps of generally equal volume and period, flow uniformity is enhanced.

For lower flow rates, the use of such supersteps can require long pauses in pump operation between the steps. A single motor step may, for example, produce a bolus of fluid which, to produce flow at the desired flow rate, requires substantial time to elapse before the next motor step occurs. Moreover, in some cases, even with long pauses between steps, a particularly large-volume step may cause the system to momentarily exceed the desired flow rate. The problem of such large-volume steps could be increased by the use of supersteps that consist of more than one step.

Various modifications to fluid pump drive systems can be made to address uniformity at low flow rates, including the addition of a gear train and/or development of a pump having a greater number of steps per revolution. Such modifications can, however, be expensive in that they typically require development of an entirely new pump mechanism.

In part to address concerns for low flow rates, a motor drive technique known as "microstepping" was developed, wherein each motor step was subdivided into a series of smaller microsteps. For example, each motor step might be subdivided into up to eight different microsteps. Those microsteps could then be grouped into "packets" of microsteps, with each packet having essentially the same volume as other packets.

Microstepping has been found to increase flow uniformity and significantly reduce motor noise. Microstepping involves driving the step motor through a step with a series of current magnitude states that generate small angular displacements of the field vector position. The sum of these displacements equals that of one step. Because instantaneous torque is approximately a sinusoidal function of angular displacement of a motor's field vector position from its rotor position, a smaller angular displacement results in a lower instantaneous torque. A lower instantaneous torque generates an angular acceleration at the leading edge of each "microstep" smaller than that generated at the leading edge of each step in "full step" drive mode. The effect is to spread the large acceleration that normally occurs at the beginning of a step over the entire step as a series of small accelerations, thus reducing the level of acoustic noise. Thus, rather than turning through an entire step in near-instantaneous fashion, the motor can instead moves through a series of distinct incremental microsteps, each of which involves only a portion of the movement turn of an entire step.

Several existing systems make use of microsteps in various drive motors, including fluid pump motors. For example, U.S. patent application Ser. No. 08/526,468 to Holdaway, entitled "OPEN-LOOP STEP MOTOR CONTROL SYSTEM," which is incorporated herein by reference in its entirety, describes using microsteps in driving an infusion pump step motor.

In existing implementations, the duration of each microstep was typically fixed at a nominal value, such as 2.36 milliseconds. An entire packet of microsteps would often be made in relatively rapid succession, followed by a "non-flow time" during which no motor movement would occur. The average flowrate was adjusted by reducing or increasing the volume in the packets (i.e., by adjusting the number of microsteps in each packets), and also by adjusting the non-flow time (i.e., the time between microsteps in which the motor was not moving).

The non-flow period could be actively varied in order to change the average flow rate as well as to enhance other system functions. For example, U.S. patent application Ser. No. 08/688,698 to Butterfield, entitled FLUID FLOW RESISTANCE MONITORING SYSTEM, which is incorporated herein by reference in its entirety, describes a system that varies fluid delivery, including non-flow periods, using a pseudorandom code. For very low flow rates, the non-flow time might become relatively large. For example, a desired flow rate of 0.1 ml/hr might involve a non-flow period on the order of 200 seconds.

In fluid driving systems, there are circumstances wherein maximum flow uniformity is desirable. For example, in parenteral infusion of some fluids that require very low flow rates, such as certain fast acting (i.e., short half-life) drugs, it can be desirable to maintain minimal fluctuation of the instantaneous flow rate. This need for minimal fluctuation of the flow rate can become most acute in the lower ranges of flow typically produced by commercial peristaltic infusion devices, such as the range from 0.1 to 1.0 ml/hr.

Some organizations, such as the Emergency Care Research Institute (ECRI), have promulgated ratings of flow uniformity based on the interval between "flow steps" at the lowest flow rate achieved. Such ratings, although typically somewhat indefinite, can provide useful guidelines. For example, ECRI rates an infusion pumps flow uniformity as "excellent" if less than 20 seconds elapse between "flow steps" at the "lowest rate programmable." Assuming that the ECRI rating is based on having steps of equal volume, many current commercial devices are far from meeting such criteria.

Hence those skilled in the art have recognized the need for increasing flow uniformity, particularly at low flow rates. The present invention fulfills these needs and others.

SUMMARY OF THE INVENTION

Briefly, and in general terms, the present invention provides a system and method for controlling the flow of fluid in a conduit acted on by a pumping mechanism by controlling the movement of the pumping mechanism to obtain increased flow uniformity. In one aspect, a system for controlling the flow of fluid through a conduit in response to a selected flow rate to provide more uniform flow is provided wherein the system comprises a pumping mechanism acting on the conduit to control the flow of the fluid through the conduit, the pumping mechanism including a plurality of pumping devices that compress the conduit in a predetermined pumping pattern to cause fluid movement through the conduit, the mechanism moving in successive steps of movement of the pumping devices through a complete pumping cycle. Included is a memory in which is stored a quantity of fluid that flows through the conduit corresponding to each movement step of the pumping mechanism; and a processor is adapted to select and group successive steps of movement of the pumping devices in packets to pump as close to the target flow volume as possible in each packet of steps; the processor being further adapted divide the steps into microsteps and to cause the pump motor to drive through the microsteps so as to having within each packet microsteps with equal periods to the other microstep periods in that packet.

In a further aspect, the pumping mechanism moves through the microsteps assigned to each packet during all or substantially all of the packet time period, so that the waiting period during which the mechanism does not move is minimized or eliminated.

In a more detailed aspect, the pumping mechanism comprises a step motor driving the pumping devices into and out of contact with the fluid conduit in the predetermined pattern to cause fluid to flow through the conduit, the memory stores a volume of fluid flow through the conduit that corresponds to each step of the step motor, wherein the processor controls the step motor to move in movement microsteps having microstep periods that are determined as a function of the flow volume for the microstep period and in the particular packet.

In yet another aspect, the processor selects the microstep period based on the flow rate, with the length of the microstep period selected being inversely proportional to the flow rate selected.

In yet another aspect, the pumping mechanism passes at high or maximum speed through a series of pump steps during which the sum total flow is essentially zero.

Other features and advantages of the invention will become apparent from the following detailed description, taken in conjunction with the accompanying drawings, which illustrate, by way of example, the features of the invention.

DETAILED DESCRIPTION OF THE PREFERRED EMBODIMENTS

Figure 1:
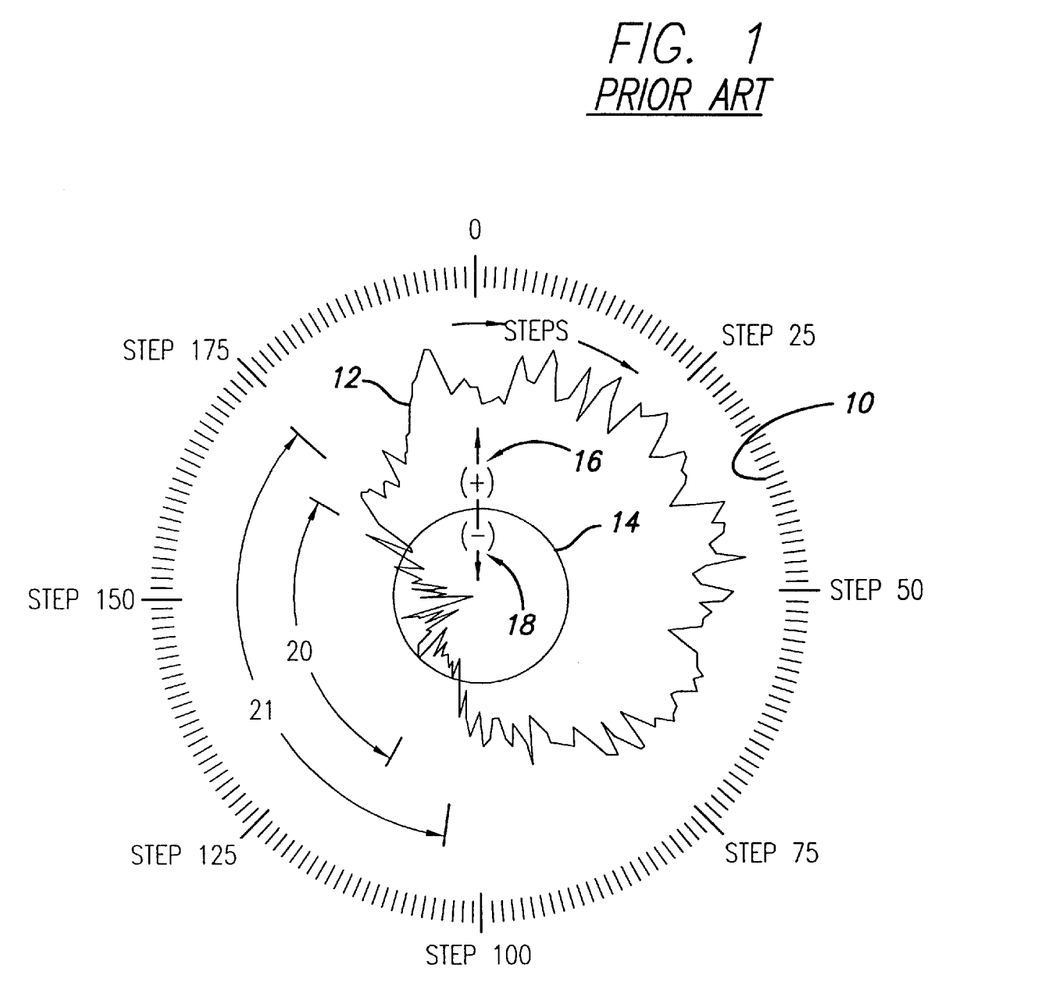
FIG. 1 is a polar graph of the volume pumped per motor step over one pump cycle of a common linear peristaltic pump.
Figure 2:
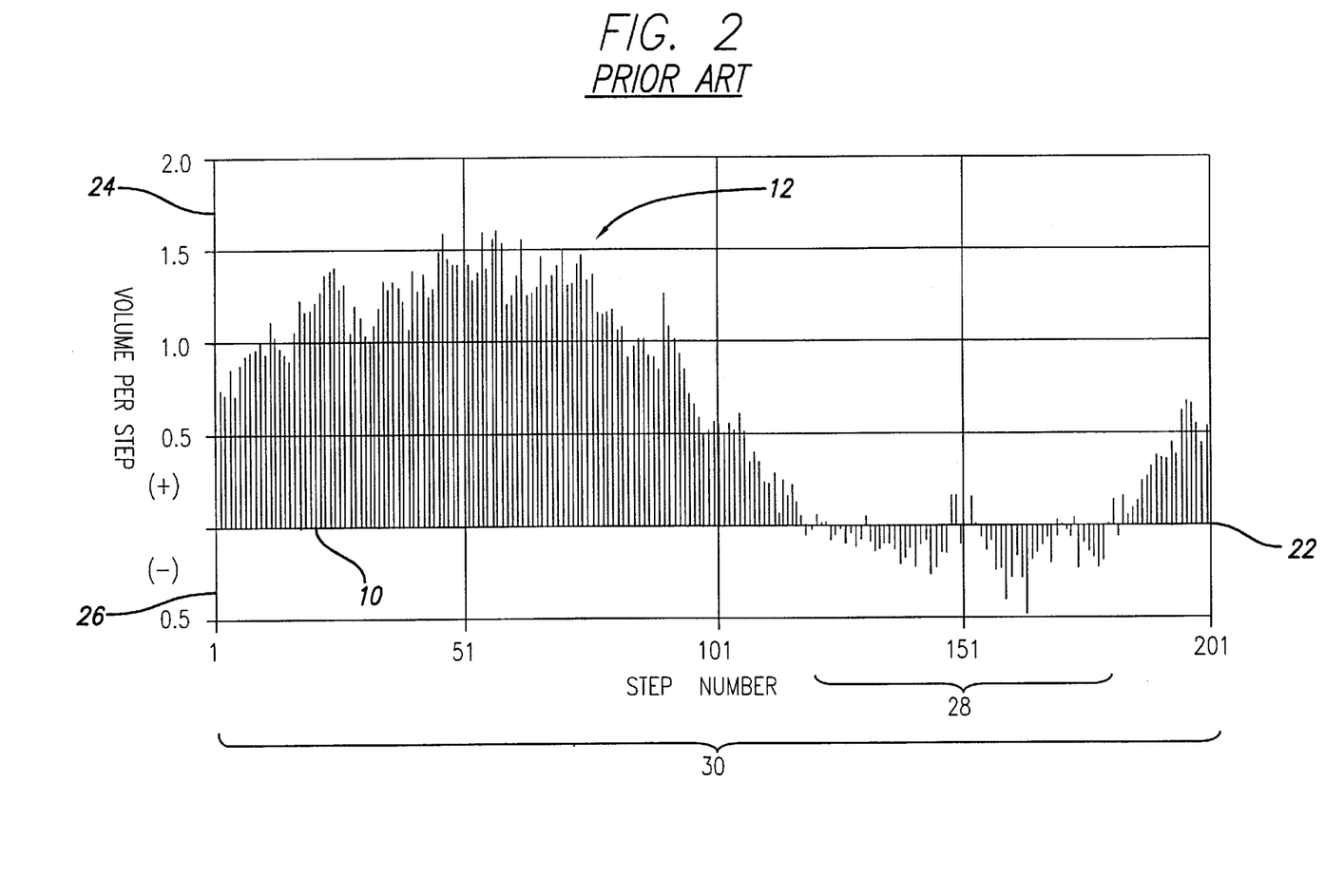
FIG. 2 is a linear graphical representation of the pump cycle shown in FIG. 1.

Referring now to the drawings with more particularity, wherein like reference numerals in the separate views indicate like or corresponding elements, there is shown in FIGS. 1 and 2 a pump cycle flow pattern for a typical linear peristaltic pump, with the pump having a motor cycle of 200 steps. FIG. 1 shows a polar graph of the pump cycle flow pattern, while FIG. 2 shows a linear graph of the same pattern.

In FIG. 1, individual motor steps 10 are shown beginning at a reference point "0" and sequentially move in equal angular increments in a clockwise direction over a complete 200-step rotation returning to the reference point "0". The pump cycle flow pattern 12 results. Zero flow is represented by a circle 14, positive flow 16 is represented outside the circle, and negative flow 18 is represented inside the circle. A net reverse or negative flow period is illustrated by the arc 20, with a net zero flow period illustrated by the arc 21. By referring to the portion of the pattern corresponding to a particular motor step, the volume pumped by that step (step volume) can be determined. Step volumes can be determined by means well known to those skilled in the art, such as by gravimetric measurement.

FIG. 2 presents the same data as FIG. 1 except in a linear graphical format. Individual motor steps 10 are shown beginning at a reference point "0" defined at the intersection of the X and Y axes and each subsequent motor step is represented along the X-axis. The pump cycle flow pattern 12 resulting from the individual step volumes pumped corresponding to each motor step rotated is shown. Zero flow is represented by the X-axis 22, positive flow is represented by the positive Y-axis 24 and negative flow is represented by the negative Y-axis 26. A net reverse or negative flow period 28 is also illustrated. As is apparent from an observation of both FIGS. 1 and 2, different volumes are pumped per step during the pump cycle 30.

Figure 3:
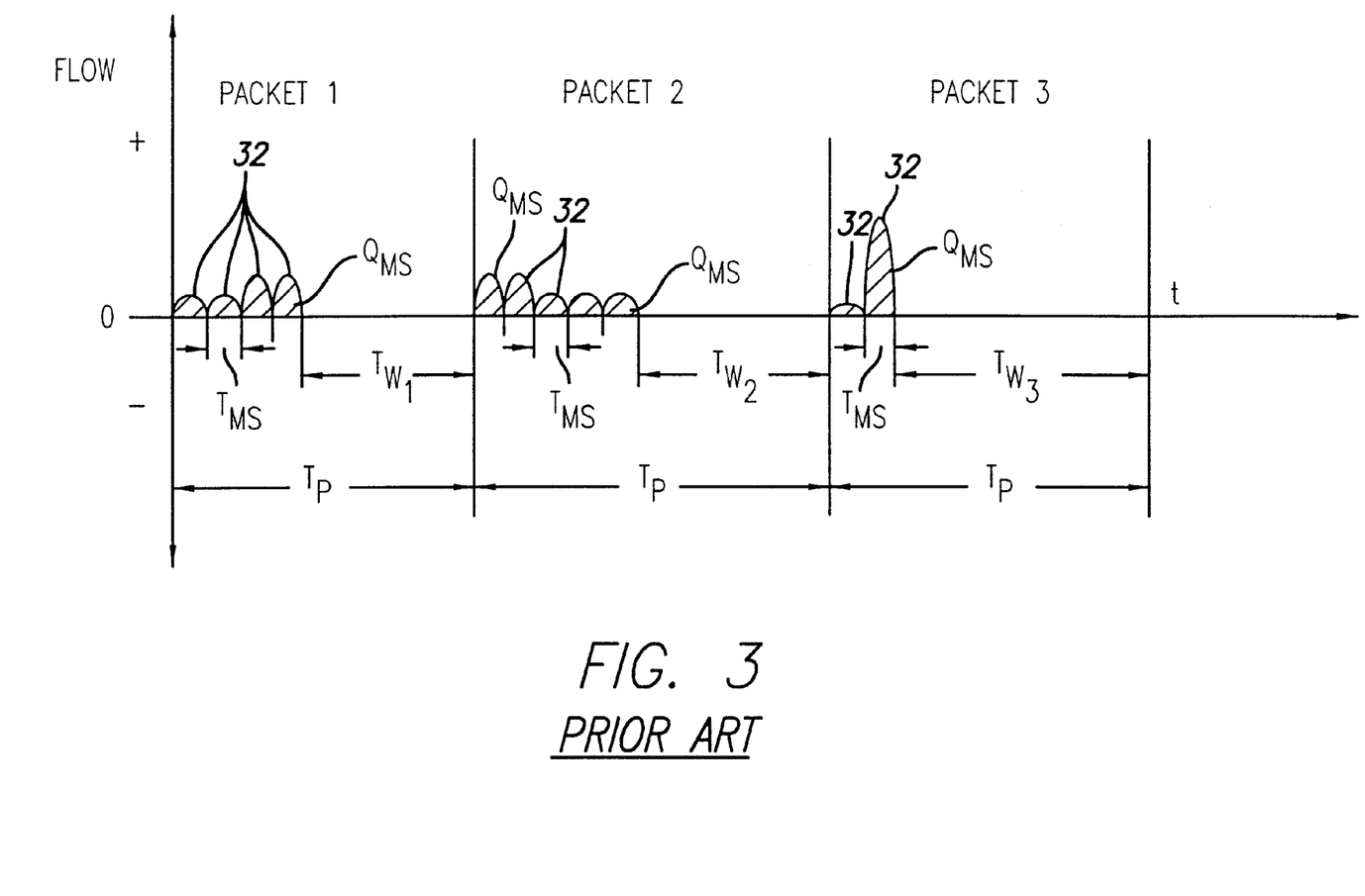
FIG. 3 is a graphical representation of fluid flow superimposed over packet time periods with a substantial waiting period.

Increased flow uniformity can be achieved by dividing motor steps into microsteps and then grouping those microsteps into "packets" having equal periods $T_P$ and generally equal fluid volumes $Q_P$, as set forth in FIG. 3. In the embodiment depicted in FIG. 3, three adjacent packets are composed of four, five, and two microsteps 32, respectively. The area under each microstep corresponds to the fluid flow volume $Q_{MS}$ for that microstep, with the sum of the fluid flow volumes within each packet (i.e., $Q_P$) being approximately the same as the total volume for the other packets.

Note that the grouping or "packetizing" may actually be conducted at the step level, whereby different steps are assigned to packets, and the steps are then broken into smaller microsteps within the packet. Because different steps and microsteps can have different volumes $Q_S$, $Q_{MS}$, the number of steps and microsteps can vary from packet to packet to maintain generally equal packet fluid volumes $Q_P$. The packet volume $Q_P$ for a particular packet is thus defined as the sum of all step and/or microstep volumes in that packet, as follows:

$$Q_P = \Sigma Q_S \qquad (1)$$

or $$Q_P = \Sigma Q_{MS} \qquad (2)$$

Because of variations in the step and microstep volumes, the packet volume is usually not precisely equal from packet to packet. However, by carefully selecting and grouping the steps and/or microsteps for each packet, the packet volume $Q_P$ can be held relatively constant from packet to packet, even where the step and microstep volumes $Q_S$, $Q_{MS}$ vary widely.

In one embodiment of the invention, packets are assigned at the step level, and the steps are then divided into microsteps. In a further embodiment, different steps may be divided into different numbers of microsteps. For example, the first step in a packet may be divided into an initial large number of microsteps, the second divided into half as many microsteps, the third into one-fourth as many microsteps, and so on, with the number of microsteps per step decreasing until a single microstep per step is used. At the end of the packet, the process is reversed, with the third-to-last step being divided into the same number of steps as the third step, the second-to-last being divided into the same number of microsteps as was the second step, and the last step being divided into the same initial large number as was the first step. As an example of such an embodiment, in a packet of 9 steps, the steps are broken into microsteps as set forth in Table A:

| STEP # | NUMBER OF CORRESPONDING MICROSTEPS |
|---|---|
| 1 | 8 |
| 2 | 4 |
| 3 | 2 |
| 4 | 1 |
| 5 | 1 |
| 6 | 1 |
| 7 | 2 |
| 8 | 4 |
| 9 | 8 |

Noted that the particular embodiment depicted in Table A has a set limit of eight for the number of microsteps into which any step can be divided.

In another embodiment, each step may be divided into the same number of microsteps. For example, all steps might be divided into 4 microsteps.

In typical infusion systems, the pump motor rapidly advances through each microstep, so that microsteps 32 each have fixed, generally identical (and relatively small) periods $T_{MS}$, as shown by way of example in FIG. 3. Microstep periods for typical pumps are on the order of just a few milliseconds. Thus, in order to achieve the desired flow rate while maintaining a generally constant packet period $T_P$, a relatively large waiting period of pump inactivity $T_W$ can be used to extend the packet period $T_P$ to the desired value. In such systems, the waiting period $T_W$ varies from packet to packet, depending on the number of microsteps in the packet. As was discussed previously, for low flow rates the waiting period $T_W$ can become quite large when the microstep periods $T_{MS}$ are small. For example, for a flow rate of 0.1 ml/hr can involve a waiting period $T_W$ (i.e., non-flow period) on the order of 200 seconds.

Figure 4:
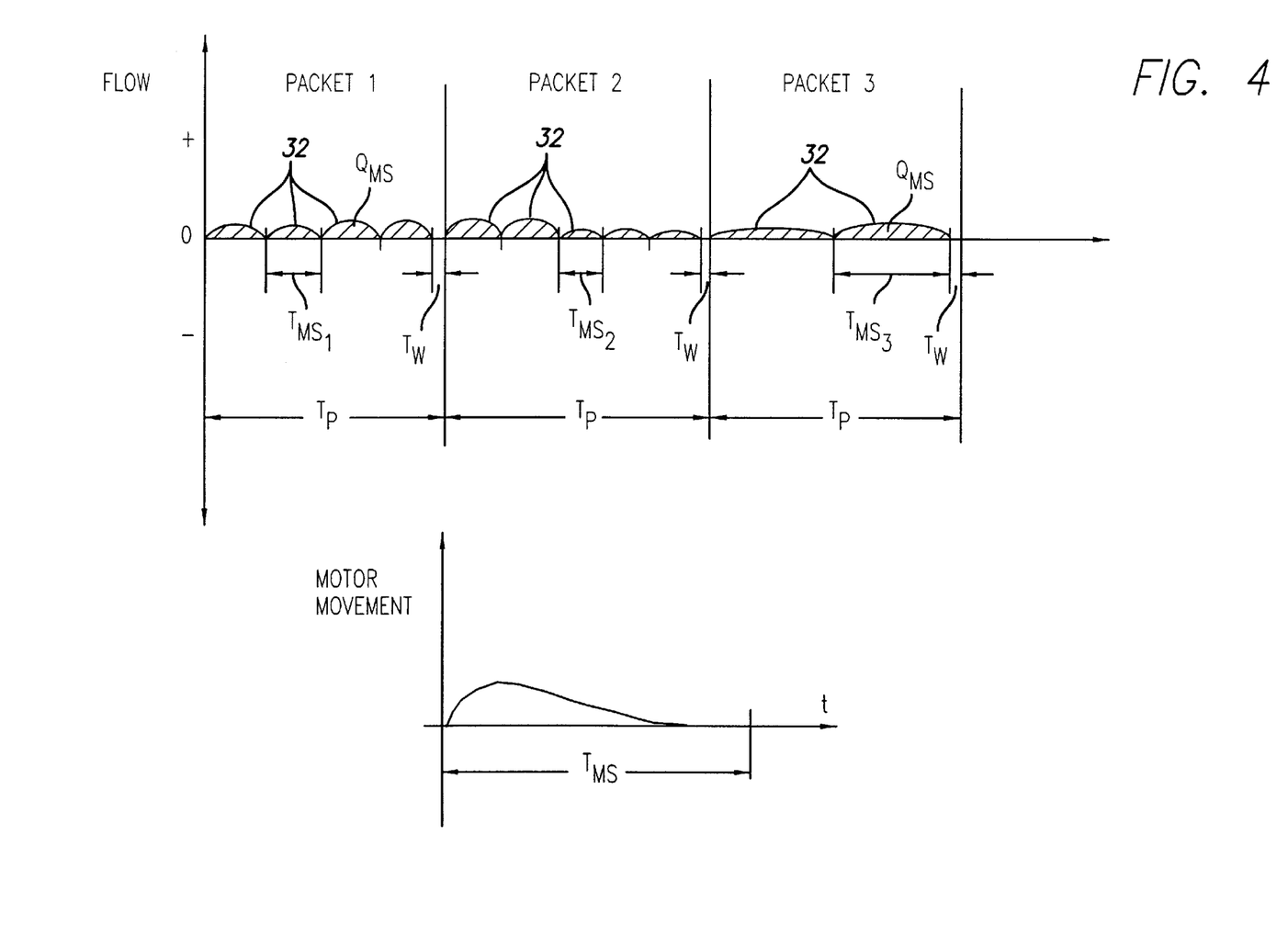
FIG. 4 is a graphical representation of fluid flow superimposed over packet time periods where the waiting period is relatively small.

As depicted in FIG. 4, the current invention eliminates or minimizes the waiting period $T_W$ by enlarging the individual microstep periods $T_{MS}$. By controlling the pump motor to very slowly pass through the microsteps, the microstep periods $T_{MS}$ are extended so that, in total within a packet, they encompass all or substantially all of the packet period $T_P$, thereby eliminating or at least minimizing the waiting period $T_W$. Note that the motor may not actually be moving during the entirety of each microstep period $T_{MS}$. Due to the mechanical and electrical characteristics and behavior of step motors, microstep movement is usually not consistent throughout the microstep period $T_{MS}$. For example, as depicted in FIG. 4a, the microstep may involve substantial motor movement at the very beginning of the microstep period $T_{MS}$, with that movement slowing down afterward so that toward the end of the microstep period $T_{MS}$ there may in fact be little or no movement of the motor. This time of non-movement is generally small, however, and does not create substantial non-flow times.

In an embodiment of the invention, the waiting period $T_W$ at the end of each packet is not completely eliminated, but is instead brought down to a very low value. In a further embodiment, the waiting period $T_W$ is held generally constant, preferably at a very low value, from packet to packet. This is in contrast to systems that hold the step or microstep period $T_{MS}$ constant and instead vary the waiting period $T_W$ to achieve desired flow rates.

In the particular embodiment of FIG. 4, the waiting period $T_W$ is so small as to almost negligible. The microstep periods $T_{MS}$ are generally constant within each particular packet, with the microstep periods $T_{MS}$ in a packet generally equal to the packet period $T_P$ divided by the number of microsteps in that period. For example, in Packet 1 from FIG. 4, there are 4 microsteps, so that each microstep period $T_{MS1}$ is equal to or about ¼ of the total packet period $T_P$. For packet 2, which has 5 microsteps, the microstep period $T_{MS2}$ is equal to about ⅕ of the total packet period $T_P$. Thus, the microstep period is generally defined as follows:

$$T_{MS}=T_P/n_{MS} \quad (3)$$

where $n_{MS}$ is the number of microsteps in the packet.

In an alternate embodiment, the microstep period could be determined for each microstep individually, possibly taking into account the volume delivered in the particular microstep. As an example, the microstep period $T_{MS}$ may be a function of the total packet period $T_P$, the total volume delivered in the packet $Q_P$, and the volume delivered by the particular microstep $Q_{MS}$. An equation such as the following might be employed:

$$T_{MS}=T_P*(Q_{MS}/Q_P) \quad (4)$$

Information regarding the volumes $Q_{MS}$ and/or $Q_P$ might be held in a table that the system processor consults for the various steps and microsteps.

To increase the flow rate, the system can increase the number of microsteps in each packet (thereby increasing the packet volume $Q_P$). Alternatively (or additionally), the system can increase the flow rate by decreasing the packet period $T_P$. To decrease the flow rate, the system can decrease the number of microsteps per packet and/or increase the packet period $T_P$.

In a preferred embodiment of the invention, the packet volume $Q_P$ (and therefore the number of microsteps) in each packet is held at a generally constant value for all flow rates in specific range. In a more specific embodiment, the packet volume $Q_P$ is maintained at the 5–μl level for flow rates under 50 ml/hr. By maintaining the packet volume $Q_P$ generally constant, the system does not have to redetermine the appropriate number of microsteps for each packet every time the flow rate is changed.

In a typical pump mechanism having 200 steps per revolution, one revolution of the pump mechanism usually delivers in the range of about 165 to 200 microliters. Thus, it takes about five or so complete revolutions of the pump mechanism to deliver a milliliter of fluid. These five or so complete revolutions involve over 1000 steps, so that delivery of a milliliter of fluid is spread across over 1000 steps. However, due to the physical characteristics and operation of most peristaltic devices, a significant number of back-to-back steps in each revolution do not, in total, produce significant fluid flow. For example, in the pump cycle flow pattern depicted in FIG. 1, the arc identified as 21 produces, in total, essentially zero fluid flow. Rather than try to apportion these series of low or even negative flow steps out across various packets, it has been found to be effective to simply run the motor at maximum or relatively high speed through the series of steps in arc 21. For example, the series of steps in the zero sum fluid flow arc might be traversed by the pump in a very short time, on the order of 100 milliseconds. Because the sum total of the flow in the series of steps in arc 21 is zero, such a rapid advancement through those steps helps to enhance the flow uniformity.

Figure 5:
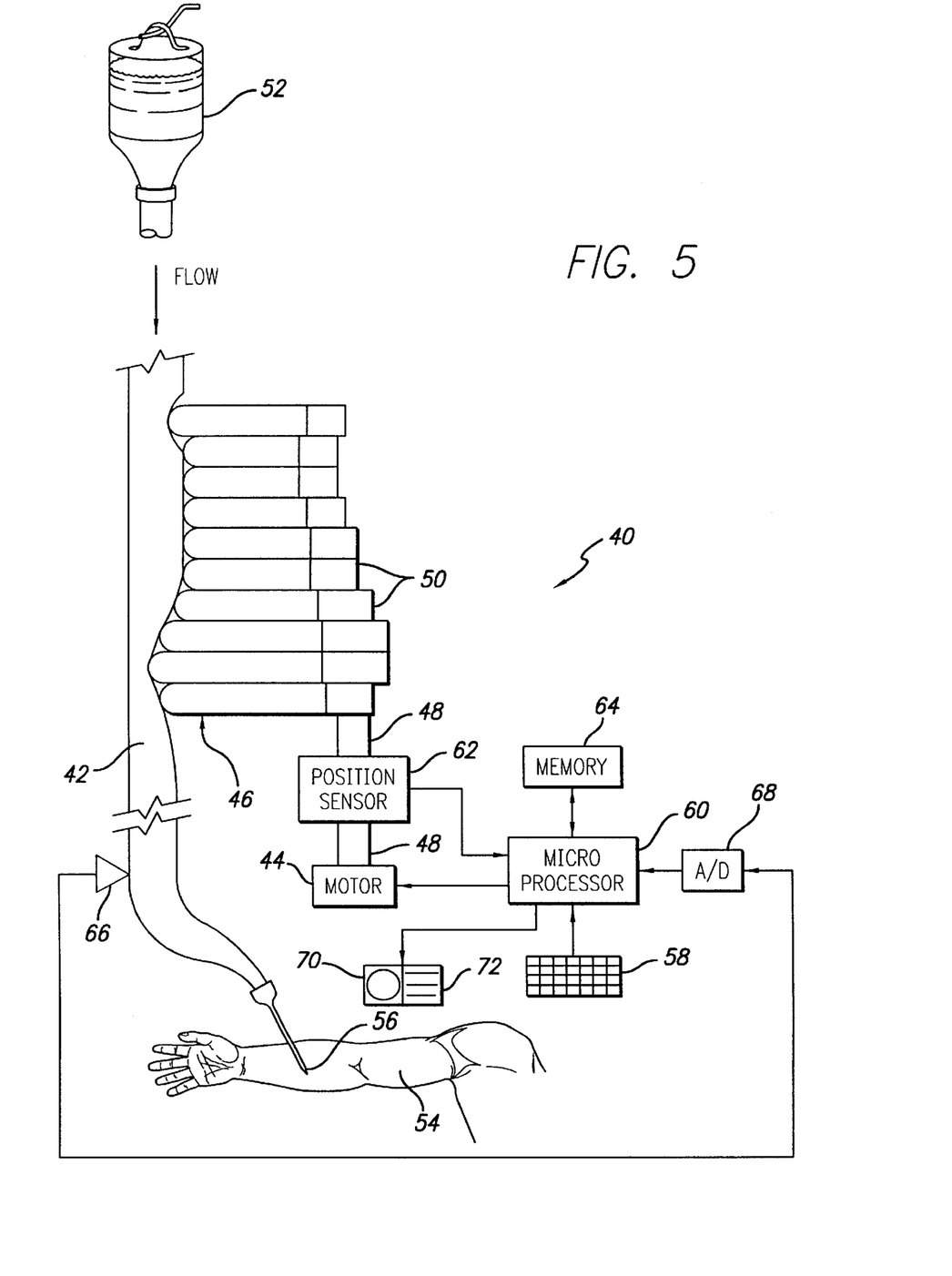
FIG. 5 is a schematic illustration of a linear peristaltic fluid delivery system embodying features of the invention and employing a position sensor and step motor under processor control to move parenteral fluid from a fluid reservoir to a patient.

FIG. 5 is a block diagram of a fluid delivery system 40 incorporating aspects of the current invention. The fluid delivery system includes a fluid delivery conduit 42 acted upon by a pumping mechanism 46 driven by a pump motor 44. In the embodiment shown, the pumping mechanism 46 comprises a rotating cam shaft 48 coupled to the pump motor 44 and moving a series of peristaltic elements 50. The peristaltic elements 50 operate on the conduit 42 to move fluid from a fluid source 52, through the conduit 42, and into a patient 54 via a cannula 56.

A user input device 58, such as a keypad, provides operator instructions, such as flow rate selection, to a processor 60. The processor 60 controls the operation of the pump motor 44 driving the pumping mechanism 46. A motor position sensor 62 determines the position of the motor 44 and pumping mechanism 46 and provides a position signal to the processor 60. A memory 64 may be provided to store and provide appropriate information, such as tables of information relating to volume per step and/or microstep.

The system may include various elements for monitoring system parameters, such as those set forth in pending U.S. patent application Ser. Nos. 08/688,698 and 08/526,468. For example, the system may include a pressure sensor 66 coupled to the conduit 42 to sense pressure in the conduit. An analog-to-digital converter 68 ("A-to-D") receives the analog pressure output signals from the sensor 66 and converts them to a digital format at a particular sample rate controlled by the processor 60. The processor 60 receives the digital pressure signals, processes them as described in more detail below and calculates the resistance to flow. A display 70 may be included to present system information, such as resistance or flow rate, and one or more alarms 72 may be provided to indicate an unsatisfactory operational parameter.

In the embodiment depicted in FIG. 5, the selection of a flow rate is made at the keypad 58 and is received by the processor 60. The user may also select at the keypad 58 between operational modes, such as variable pressure mode (for low flows where high flow uniformity is critical) and resistance monitoring mode (such as the resistance monitoring mode described in pending U.S. patent application Ser. No. 08/688,698).

A fluid delivery system in accordance with the current invention may include one or more modes of operation, with use of the increased flow uniformity elements and method steps only allowed during certain of the operational modes. For example, a fluid delivery system may have a first mode, such as a resistance monitoring mode, during which monitoring of system parameters such as resistance might be interfered with by the uniformity elements and methods. Accordingly, the system might prohibit use of the heightened flow uniformity elements and methods during operation in the first mode. Such a fluid delivery system may have a second mode, such as a variable pressure mode, during which the system permits operation of the uniformity elements and methods.

In a preferred embodiment, the system will not allow the user to select incompatible combinations of flow rates and operational modes. For example, in a particular embodiment, the use of a heightened flow uniformity mode may be restricted to flow rates of 50 ml/hr or less. Accordingly, the system would not allow the user to select a combination of a heightened flow uniformity mode with a flow rate over 50 ml/hr.

While the invention has been illustrated and described in terms of certain preferred embodiments, it is clear that the invention can be subject to numerous modifications and adaptations within the ability of those skilled in the art. Thus, it should be understood that various changes in form, detail and usage of the present invention may be made without departing from the spirit and scope of the invention.

What is claimed is:

1. An apparatus for increasing the uniformity of flow of fluid through a conduit comprising:
    a drive device that moves in movement increments;
    a pumping mechanism coupled to the drive device that pumps fluid through the conduit in volume increments in response to movement increments of the drive device, with each volume increment corresponding to a respective movement of the drive device, at least some of the volume increments differing from other volume increments;
    an input device that provides a desired flow rate value;
    a processor configured to:
        receive the desired flow rate value;
        group the movement increments into movement groups as a function of the volume increments corresponding to the respective movement increments, with each movement group having a total flow volume equal to the combined volume increments of the movement increments in the movement group, wherein the total flow volumes of all movement groups are approximately equal, and wherein the total flow volume of each movement group is a generally constant value for all desired flow rates within a specific range of flow rates and the total flow volume of each movement group is a function of the desired flow rate for flow rates outside the specific range of flow rates;
    assign a group period to each movement group as a function of the desired flow rate, wherein the group periods of all movement groups are equal;
    determine an increment period for each movement increment, wherein the combined increment periods of all movement increments in a movement group are approximately equal to the group period for the movement group; and
    control the drive device to move in the movement increments, with the movement increments occurring at the assigned increment periods.

2. The apparatus of claim 1 wherein the processor is configured to control the drive device to cause the movement increment period of each movement increment within an increment group to be proportional to the fluid flow volume increment of the movement increment.

3. The apparatus of claim 1 wherein the processor is configured to control the drive device to cause the movement increment period of all movement increments within an increment group to be equal.

4. A parenteral fluid delivery system comprising:
    a fluid delivery conduit;
    a peristaltic pump, said pump having a plurality of peristaltic elements movable into and out of engagement with the conduit to control the flow of fluid through the conduit;
    a drive device having a plurality of positions through which the drive device may move in incremental movements, said drive device coupled to the peristaltic elements of the pump, wherein the peristaltic elements pump fluid through the conduit in volume increments in responses to incremental movements of the drive device, each volume increment corresponding to a respective incremental movement of the drive device;
    a position sensor that monitors the position of the drive device;
    a memory that is configured to store data representing the volume increment of fluid flow corresponding to each incremental movement of the drive device;
    an input device that provides a desired move selection; and
    a processor in communication with the memory, said processor configured to receive the desired mode selection and select one of two or more operational modes, the processor in at least one, but not all, of said operational modes further configured to:
    receive the drive device position signal and the fluid flow volume increment data;
    assign incremental movements of the drive motor to incremental movement groups as a function of the fluid flow volume increment data for each incremental movement, with the combined fluid flow volume increments of all incremental movements within a movement group approximately equal to the combined fluid flow volume increments of other movement groups;
    assign a timeslot for each incremental movement group, with all timeslots having an equal period; and control the drive device to cause the movement increments in each movement group to be spread across the timeslot period for that movement group, with each movement increment having a period, with the sum of all movement increment periods in a movement group being equal to the movement group period.

5. The apparatus of claim 4 wherein the processor is configured to control the drive device to cause the movement increment period of each movement increment within an increment group to be proportional to the fluid flow volume increment of the movement increment.

6. The apparatus of claim 4 wherein the processor is configured to control the drive device to cause the movement increment period of all movement increments within an increment group to be equal.

7. The apparatus of claim 4 wherein the processor is configured to continuously move at high or maximum speed through a predetermined number of movement increments, the sum total of the increments of fluid flow indicated in memory corresponding to the respective movement increments being essentially zero.

8. The apparatus of claim 4 wherein the drive device comprises a cam shaft rotated by a step motor, said step motor moving in a series of motor steps, with each motor step corresponding to a movement increment.

9. The apparatus of claim 4 wherein the drive device comprises a cam shaft rotated by a step motor, said step motor moving in a series of motor steps, with said motor steps further divided into microsteps, wit each microstep corresponding to a movement increment.

* * * * *